(12) United States Patent
Ascher et al.

(10) Patent No.: US 12,648,735 B2
(45) Date of Patent: Jun. 9, 2026

(54) CURVED ULTRASOUND PROBE

(71) Applicant: THINKIN TECH, Paris (FR)

(72) Inventors: Benjamin Ascher, Paris (FR); Boris Vaynberg, Zichron Yakov (IL)

(73) Assignee: THINKIN TECH, Paris (FR)

( * ) Notice: Subject to any disclaimer, the term of this patent is extended or adjusted under 35 U.S.C. 154(b) by 0 days.

(21) Appl. No.: 18/684,726

(22) PCT Filed: Aug. 17, 2022

(86) PCT No.: PCT/EP2022/073002
§ 371 (c)(1),
(2) Date: Feb. 19, 2024

(87) PCT Pub. No.: WO2023/021110
PCT Pub. Date: Feb. 23, 2023

(65) Prior Publication Data
US 2024/0350085 A1      Oct. 24, 2024

(30) Foreign Application Priority Data
Aug. 17, 2021      (EP) ..................................... 21315138

(51) Int. Cl.
*A61B 5/00*          (2006.01)
*A61B 8/00*          (2006.01)
*A61B 8/08*          (2006.01)
(52) U.S. Cl.
CPC .......... *A61B 5/6826* (2013.01); *A61B 8/0891* (2013.01); *A61B 8/4227* (2013.01);
(Continued)

(58) Field of Classification Search
CPC ... A61B 5/6826; A61B 8/0891; A61B 8/4227; A61B 8/4455; A61B 8/4472; A61B 8/565; A61B 8/4411; A61B 8/4209
See application file for complete search history.

(56) References Cited

U.S. PATENT DOCUMENTS 5,152,293 A      10/1992  Vonesh et al.
5,284,147 A      2/1994   Hanaoka et al.
(Continued)

FOREIGN PATENT DOCUMENTS

WO      WO-2010073913 A1 *  7/2010   ......... A61B 5/14552

OTHER PUBLICATIONS

Kanazawa et al (WO 2010073913) machine translation (Year: 2010).*
(Continued)

*Primary Examiner* — Alexei Bykhovski
(74) *Attorney, Agent, or Firm* — CUSHMAN PARTNERS LLC

(57)          ABSTRACT
An ultrasound hand probe intended to be placed on a ventral part of a finger, configured to emit and receive ultrasound, the ultrasound hand probe including a curved ultrasound transducer, a housing attached to the curved transducer, the curved transducer being arranged on a distal end of the housing, the housing including a curved finger base including a curvature along a longitudinal axis of the ultrasound hand probe, electrical connections for: supplying power to the curved transducer, and transmitting a signal produced by the curved ultrasound transducer signal, at least one accessory device-including at least one first attach to fasten the at least one accessory with the ultrasound hand probe.

21 Claims, 4 Drawing Sheets

(52) U.S. Cl.
CPC .......... *A61B 8/4455* (2013.01); *A61B 8/4472* (2013.01); *A61B 8/565* (2013.01)

(56)                    References Cited

U.S. PATENT DOCUMENTS

| | | | |
|---|---|---|---|
| 5,598,846 A | 2/1997 | Peszynski | |
| 2004/0225217 A1 | 11/2004 | Voegele et al. | |
| 2005/0085731 A1* | 4/2005 | Miller | A61B 8/12 |
| | | | 600/459 |
| 2005/0096554 A1* | 5/2005 | Dudik | A61B 5/6826 |
| | | | 600/500 |
| 2008/0300488 A1* | 12/2008 | Schutz | A61B 90/53 |
| | | | 600/459 |
| 2009/0163807 A1 | 6/2009 | Sliwa | |
| 2013/0150725 A1 | 6/2013 | Choi | |
| 2015/0127068 A1* | 5/2015 | Simon | A61N 1/36175 |
| | | | 607/60 |
| 2015/0250451 A1* | 9/2015 | Fearnot | A61B 8/4461 |
| | | | 600/467 |
| 2019/0254627 A1 | 8/2019 | Corbett et al. | |
| 2021/0278530 A1* | 9/2021 | Haque | H10N 30/302 |

OTHER PUBLICATIONS

International Search Report as issued in International Patent Application No. PCT/EP2022/073002, dated Nov. 25, 2022.
Communication pursuant to Article 94(3) EPC as issued in European Patent Application No. 22762113.3, dated Feb. 3, 2026.

* cited by examiner

CURVED ULTRASOUND PROBE

CROSS-REFERENCE TO RELATED APPLICATIONS

This application is the U.S. National Stage of PCT/EP2022/073002, filed Aug. 17, 2022, which in turn claims priority to European patent application number 21315138.4 filed Aug. 17, 2021. The content of these applications are incorporated herein by reference in their entireties.

FIELD OF THE INVENTION

The present invention relates to the field of ultrasound probes. More precisely, the invention relates to the field of ultrasound probes for application in a surgical and medical environment, especially an ultrasound hand probe or a finger probe.

BACKGROUND OF THE INVENTION

The use of ultrasound probes to monitor medical and surgical activities is very well known by medical doctors and physicians.

An ultrasound probe emits sonic waves in the field ultrasounds in order to acquire an image of regions of interest in a patient's face and/or body. More precisely, the ultrasound sonic wave emitted by the probe is reflected by the boundaries between different layers of tissue of the body or irregularities of the acoustic impedance in the tissue, and the ultrasound device measures the time between initial and reflected signal. By knowing the speed of sound in the human tissue and the time of flight of the pulse, the software of the ultrasound device reconstructs the 2D image of tissue structure. For instance, there are substantial reflections when the waves cross the interface between different types of tissues or lesions. These measured reflections permit to acquire an image of the tissues inside the face and/or body of the patient, in the image plane of the probe. More precisely, the probe measures the time of arrival of the reflections and calculates the distance between the place of the reflection and the probe. As a result, an image of the region crossed by the ultrasounds is acquired.

It is known to use ultrasound probes in order to visualize a fetus in the womb of a pregnant woman in order to check the health of said fetus. In this kind of devices, the physician holds an ultrasound hand probe in his hand and places it on the skin of the belly of the patient. In this kind of procedure, the hand of the physician is occupied by the hand probe, avoiding him to use his hand holding the probe to do other things.

It is also known to use ultrasound hand probe to assist a physician during injection procedures. For instance, this kind of hand probe are used to visualize the tissues of the skin of the patient to detect veins and arteries and to avoid them when injecting a solution in the skin of the patient. An inconvenient of the known devices for the injection of a fluid under the skin of a patient is that the physician has to hold the ultrasound probe in its hand while injecting the fluid with the other hand. Since the procedure of injection of fluid usually requires using both hands, one holding the syringe and another one pressing or pinching the skin of the patient, the known ultrasound probe aren't as practical as they could be.

It is also known to use an ultrasound hand probe comprising a finger clip configured to attach on the finger of the physician. The finger clip enables to maintain the ultrasound probe while operating. However, this device is not practical for the physician because it maintains the probe at a place of the finger where it is hard for the physician to apply a pressure on the probe against the skin. With this probe, when the physician applies a pressure on the skin of the patient with the probe, the resulting force applied to his finger is perpendicular to the main axis of the finger. As a result, the position is inconvenient for the physician and implies fatigue to the finger and its articulations.

It is also known to use hand probes comprising a "hockey stick" shape to perform this kind of injections. This kind of probes facilitate the action of pressing the skin but don't let the second hand of the physician free to operate on the skin.

SUMMARY OF THE INVENTION

An object of the invention is to overcome the drawbacks of known ultrasound probes. The invention relates to an ultrasound probe or an ultrasound hand probe intended to be placed on the ventral part of a finger, configured to emit and receive ultrasound waves, said ultrasound hand probe comprising:

a curved ultrasound transducer,
a housing attached to the curved transducer, the curved transducer being arranged on a distal end of the housing, the housing comprising:
  a curved finger base comprising a curvature along a longitudinal axis of the ultrasound hand probe,
  electrical connections for:
    supplying power to the curved transducer, and
    transmitting a signal produced by the curved ultrasound transducer signal,
  at least one accessory device comprising at least one first attach in order to fasten said accessory with the ultrasound hand probe.

The ultrasound hand probe according to the invention provides a more convenient device for the injection procedures than the known devices. The curved finger base of the housing is adapted follow the curvature of the tip of the finger of a physician. The physician, when he presses the probe against the skin of the patient, can angle his finger relative to the surface of the skin. Thus, his finger is in the right position to apply the pression needed with the probe. As a result, the procedure of injection implies less finger fatigue for the physician and can be done more easily since the physician can have his hand in the right position.

Moreover, since the ultrasound hand probe according to the invention comprises an accessory device, multiple accessories can be attached to it, like a finger clip for example. As a result, the device is modular and can be attached on the finger of the physician to facilitate the injection procedure, or to other accessories like a stick according to the preferences of the physician. Finally, other types of accessories can be attached to the probe in order to provide other functions to the device.

According to an embodiment, the ultrasound probe is configured to perform ultrasonography in two dimensions. According to an embodiment, the ultrasound probe is configured to perform ultrasonography in three dimensions.

According to an embodiment, the ultrasound probe is configured to perform doppler exams. The ultrasound probe is a doppler probe. With a doppler probe, the user visualizes for instance the flow of blood in blood vessels. According to an embodiment, the doppler probe emits an ultrasound pulse wave.

According to an embodiment, the ultrasound probe is configured to perform elastography measurements.

According to an embodiment, the ultrasound probe is configured to perform color flow mapping.

In one embodiment, the curved finger base has a curvature along the longitudinal axis which is complementary to the curvature of the fingertip of a user. In other words, the shape of the curved finger base fits the shape of the finger pad of the user. This characteristic enables the user to press the probe on a patient by applying a force which is sensibly aligned with a longitudinal axis of the finger of the user. This reduces the fatigue of the user since the force applied is in the direction of the finger. This fatigue can lead to patholo-gies like tendinitis for the physician. It also increases the precision of the application of the probe on the surface of the skin of the patient.

In one embodiment, the curved finger base forms a contact with the distal phalanx of the finger, preferably with the distal phalanx of the index finger of the user. In one embodiment, the curved finger base forms a contact with the finger pad of the distal phalanx of the finger of the user, preferably, with the finger pad of the distal phalanx of the index finger of the user.

In one embodiment, the curved finger contacts the skin from a part which about the middle of the distal phalanx of the finger to the tip of the finger. According to an embodi-ment, the transductor is aligned with the curved finger base and the part of the finger of the user which is in contact with the finger base. According to an embodiment, the transduc-tor is aligned with the curved finger base and the part of the finger of the user which extends from a part which about the middle of the distal phalanx of the finger to the tip of the finger.

In one embodiment, the electrical connections are wires. In one embodiment, the electrical connections are cables and/or coaxial cables and/or flex cables and/or flat flex cables.

In one embodiment, at least one accessory device is a first accessory device comprising a finger clip. This characteris-tic permits the user to attach the ultrasound hand probe to his finger by simply inserting it in the finger clip.

In one embodiment, at least one accessory device is a second accessory device comprising a distal aperture con-figured to guide a needle. The aperture guiding the needle facilitate the placement of the needle in the zone scanned by the ultrasound hand probe.

In one embodiment, the distal aperture is rotatable with respect to the ultrasound hand probe, allowing to adapt an angle of injection of the needle. This permits to move the guided needle respective to the probe in order to move the zone of injection.

In one embodiment, the at least one accessory device is a third accessory device comprising a hockey stick shape. This gives another way to handle the probe, and gives the physician the possibility to choose his favourite way of using the probe.

In one embodiment, at least one accessory device is a fourth accessory device comprising a shape forming a "T" so that the ultrasound hand probe can be maintained between two fingers. Maintaining the probe between two fingers is a practical way of using the finger hand probe.

In one embodiment, the at least one accessory device comprises a rotating accessory fastener allowing a variable orientation of the housing relative to the at least one acces-sory device along a rotation axis. This characteristic gives the possibility to rotate the probe regarding the finger of the physician during utilisation. As a consequence, the physician can angle the field of view of the probe and adapt it to different situations.

In one embodiment, the rotating accessory fastener com-prises a return element allowing an automatic return of the rotating accessory fastener in its initial position.

In one embodiment, the accessory device comprises retaining wings for maintaining a finger between said retain-ing wings. This permits to attach the accessory device to the finger of the physician.

In one embodiment, the housing has an oval transversal section, an ellipse-shaped section.

In one embodiment, the housing is moulded around the curved ultrasound transducer.

In one embodiment, the curved finger base has a radius of curvature comprised between 2 centimetres and 5 centime-tres in the longitudinal plane of the ultrasound hand probe. This curvature corresponds to the curvature of the tip of a finger, thus enhancing the ergonomics of the probe.

In one embodiment, the curved finger base has a radius of curvature comprised between 1 centimetre and 5 centimetres in a transversal plane of the ultrasound hand probe. This enhances the ergonomics of the probe and facilitate its integration with the accessory device.

In one embodiment, the curved transducer has a sectorial field of view, the field of view covering an angle superior than 20 degrees. This angle of the field of view gives a good visibility to the physician when he uses the probe.

In one embodiment, the frequency of the ultrasounds emitted by the curved transducer (30) is between 10 and 30 Mhz, preferably between 18 Mhz and 20 Mhz. These values of frequency permit to scan different depths of the skin of a patient.

In one embodiment, the ultrasound hand probe is able to transmit data acquired by the ultrasound probe wirelessly, preferably with a wifi connection and/or a Bluetooth® connection. This permits to transmit wirelessly the data acquired by the probe. As a consequence, it facilitates the movements of the physician when he uses the probe.

BRIEF DESCRIPTION OF THE DRAWINGS

The above and other objects, features and advantages of the present invention will be more apparent from the fol-lowing detailed description taken in conjunction with the accompanying drawings, in which.

DETAILED DESCRIPTION OF THE INVENTION

Figure 1:
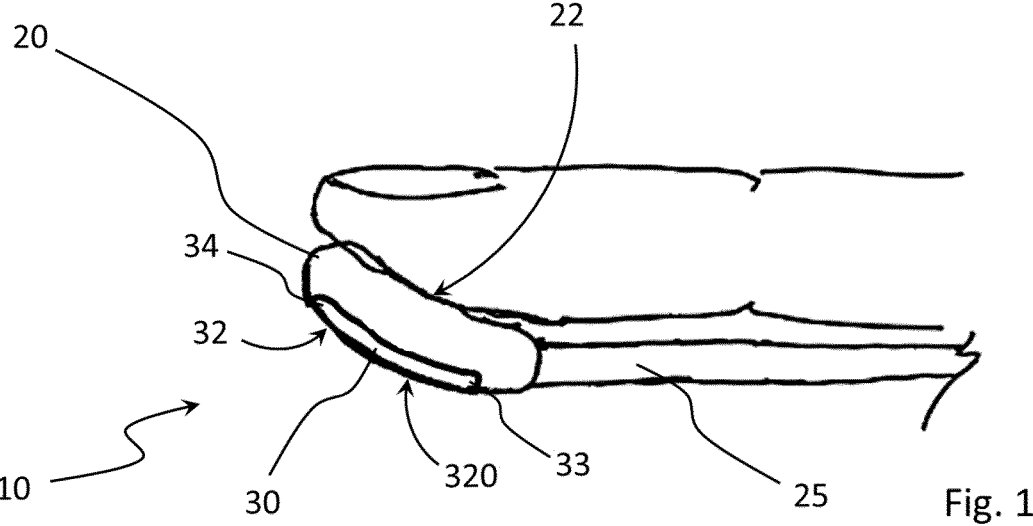
FIG. 1 is a side view of an ultrasound hand probe installed on a finger according to a first embodiment of the invention.
Figure 4:
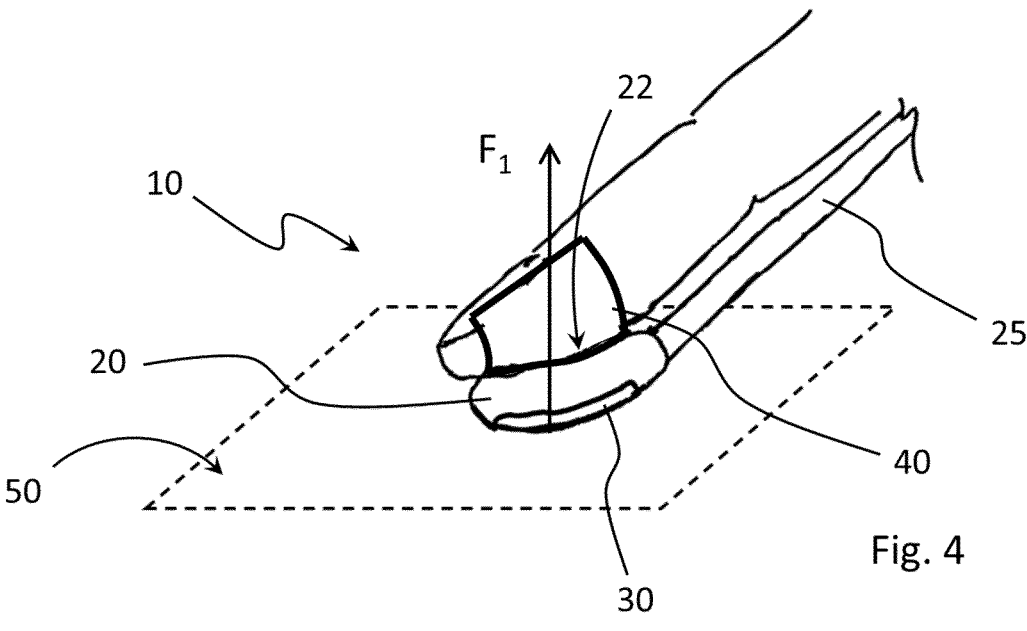
FIG. 4 is a side view of the ultrasound hand probe of FIG. 1 pressed against the surface of the skin of a patient.

FIGS. 1 and 4 depicts an exemplary ultrasound hand probe 10 according to the invention.

The ultrasound probe 10 or ultrasound hand probe 10 comprises a housing 20, a transducer 30, and at least one accessory device 40.

The Housing

Figure 2:
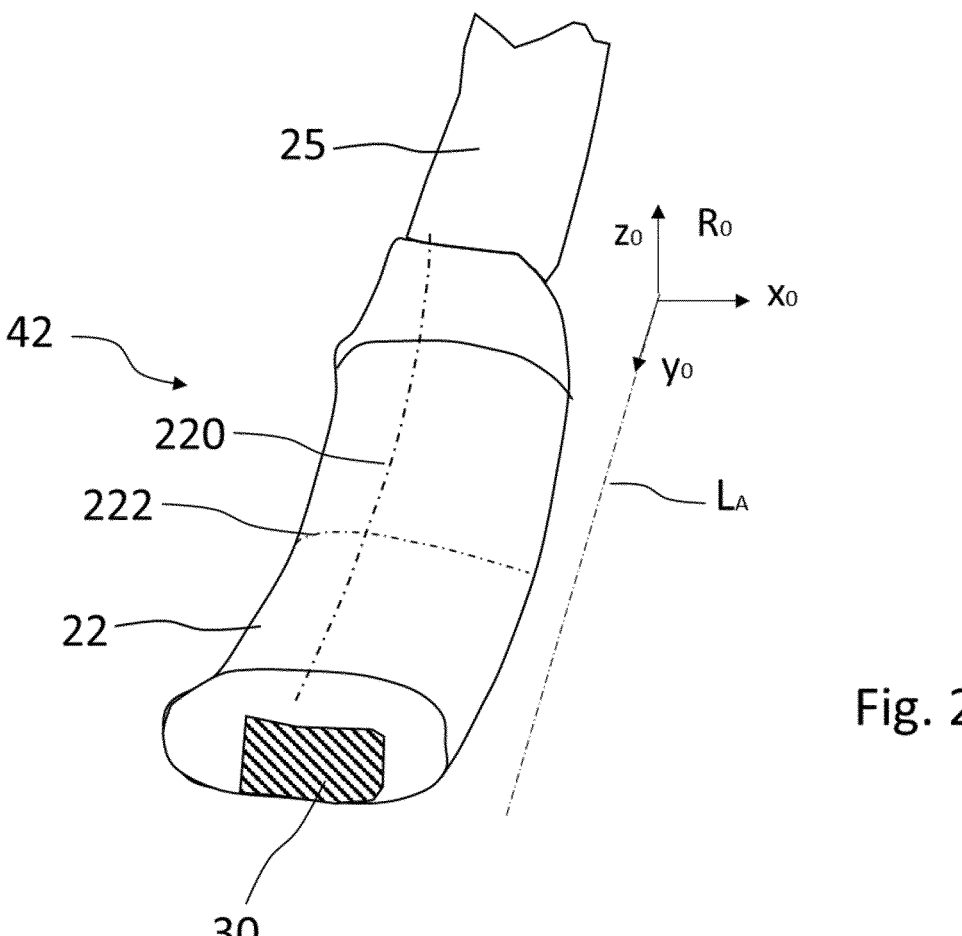
FIG. 2 is a cross sectional view of the ultrasound hand probe of FIG. 1.

The housing 20 comprises an elongated shape, as it can be seen on FIG. 2. By elongated shape, it should be understood a shape with a dimension along an axis which is substantially bigger than the dimensions of the housing 20 along the other two axes. For instance, the dimension of the housing 20 along the $y_0$ axis on FIG. 2 is substantially longer than the width of the housing 20 along the $x_0$ axis and the height of the housing along the $z_0$ axis.

The ultrasound hand probe 10 according to the invention comprises a curved finger base 22. The curved finger base 22 is curved along the longitudinal axis $L_A$ of the ultrasound hand probe 10. The curved finger base 22 comprises a main curvature 220 which is oriented along the longitudinal axis $L_A$ of the ultrasound hand probe 10. By curvature, we refer to the curvature of an external surface of the curved finger base 22.

In other words, the curved finger base has a curvature which is close to the curvature of the tip of a human finger along the main axis of said finger. As a result, the curved finger base 22 fits the shape of the fingertip of the physician. This characteristic makes the use of the finger hand probe 10 ergonomic. Since the curved base 22 fits the shape of the fingertip, the ultrasound is thus more stable on the tip of the finger than a regular straight hand probe.

The curved finger base 22 has a radius of curvature comprised between 2 centimeters and 5 centimeters. This radius is the radius of the curvature along the longitudinal axis of the finger hand probe 10. This radius corresponds to the radius that can be observed on most of the fingertips of physicians. As a result, the curved finger base 22 is fitted to the shape of the finger, making the finger hand probe more convenient to use.

According to an embodiment of the invention, the radius of curvature of the first curvature 220 of the curved finger base 22 is constant or substantially constant. In other words, the radius of curvature of the first curvature of the curved finger base 22 keeps the same curvature along its longitudinal axis.

According to another embodiment of the invention, the radius of curvature of the first curvature 220 of the curved finger base 22 can vary along the longitudinal axis of the ultrasound hand probe $L_A$. For instance, the radius of curvature is higher on a proximal end 23 of the housing 20 than it is on the distal end 24 of said housing 20. This characteristic adapts the shape of the housing to the shape of a fingertip, which has lower curvature on its proximal end than on its distal end.

Additionally, the curved finger base 22 comprises a second curvature 222. The second curvature 222 is comprised in a plane which is perpendicular to the plane comprising the first curvature 220. In other words, the second curvature 222 is perpendicular to first curvature 220. This second curvature makes it easier to interact with an accessory device which will be presented later. Additionally, the second curvature 222 is advantageously doesn't present cutting edges. This is particularly good because if the housing is inserted in a sterile glove, it doesn't risk cutting it.

Preferentially, the housing 20 has an oval transversal section. By transversal section, we refer to the section of the housing 20 in a plane which is perpendicular or substantially perpendicular to the longitudinal axis $L_A$ of the ultrasound finger probe 10. By oval section, we refer to an oval shape of said section. By oval, we refer to a shape which is in the same time round and elongated. The round parts of this section are placed on the sides of the section and the elongation of the shape is oriented along an axis perpendicular to the longitudinal axis $L_A$ pf the ultrasound hand probe 10. According to an embodiment, the housing 20 has an ellipse-shaped transversal section. By ellipse-shaped section, we refer to a section that has the shape of an ellipse, which means that contour of the section follows a curve that can be obtained by the intersection of a cone with an oblique plane that does not cut the base of the cone.

The housing 20 has a length comprised between 0.5 centimeters and 5 centimeters. Preferably, the length of the housing 20 is comprised between 1 centimeter and 3 centimeters. More preferably, the housing 20 has a length comprised between 2 centimeters and 2.5 centimeters. These values of length are these which give the size of the housing 20 which is the most convenient to use.

The housing 20 has a width comprised between 0.5 centimeters and 2 centimeters. Preferably, the width of the housing 20 is comprised between 0.7 centimeter and 1.5 centimeters. More preferably, the housing 20 has a length comprised between 0.8 centimeter and 1 centimeter. These values of length are these which give the size of the housing 20 which is the most convenient to use.

Preferably, the curved transducer 30 is integrated in the housing 20. By integrated in the housing 20, we mean that the curved transducer 30 is completely inside the housing 20, or that the curved transducer doesn't protrude from the housing 20. As a result, the assembly of the housing 20 and the transducer 30 forms a single surface, which involves no cutting edges for the assembly.

Preferably, the housing 20 is manufactured by a process of injection molding. Injection molding is a convenient and cheap way of manufacturing the housing 20. Preferably, the curved transducer 30 is integral to the housing 20. Preferably, the housing 20 is glued to the curved transducer 30. Alternatively or additionally, the housing 20 is assembled with the curved transducer 30 by potting. Alternatively, the housing 20 is 3D printed or machined to the curved transducer 30 size.

The Curved Ultrasound Transducer

In one embodiment, the curved ultrasound array transducer 30 is configured to emit and receive ultrasounds along the longitudinal axis $L_A$ of the ultrasound hand probe 30. In one embodiment, the curved ultrasound array transducer 30 is a curved linear array ultrasound transducer. The ultrasound transducer 30 is configured to receive ultrasounds. More precisely, it receives all kinds of ultrasounds and in particular the reflections of the ultrasound pulses emitted by the transducer 30. The curved ultrasound transducer 30 products a signal which is translated to an image of the ultrasound received by the transducer. It is this signal that permits to visualize the tissues under the skin of the patient.

The curved ultrasound transducer 30 comprises preferentially an elongated shape, as it can be seen on FIG. 1. By elongated shape, it should be understood a shape with a dimension along an axis which is substantially bigger than the dimensions of the curved ultrasound transducer 30 along the other two axes. For instance, the dimension of the curved ultrasound transducer 30 along the $y_0$ axis on FIG. 2 is substantially longer than the width of the curved ultrasound transducer 30 along the $x_0$ axis and the height of the housing along the $z_0$ axis.

The curved ultrasound transducer 30 is curved along the longitudinal axis $L_A$ of the ultrasound hand probe 10. The curved ultrasound transducer 30 comprises a main curvature 320 which is oriented along the longitudinal axis $L_A$ of the ultrasound hand probe 10. By curvature, we refer to the curvature of an external surface of the curved ultrasound transducer 30.

In other words, the curved ultrasound transducer 30 has a curvature 320 which is close to the curvature of the tip of a human finger along the main axis of said finger. As a result, the curved ultrasound transducer 30 fits the shape of the fingertip of the physician. This characteristic makes the use of the finger hand probe 10 ergonomic. Since the curved base 22 fits the shape of the fingertip, the physician can press the curved ultrasound transducer 30 on the skin of a patient as if it were the tip of his own finger. Additionally, he can roll the curved transducer 30 on the surface of the skin of a patient in order to vary the orientation of the curved transducer 30.

The curved ultrasound transducer 30 has a radius of curvature comprised between 2 centimeters and 5 centimeters. This radius is the radius of the curvature along the longitudinal axis of the finger hand probe 10. This radius corresponds to the radius that can be observed on most of the fingertips of physicians.

According to an embodiment of the invention, the radius of curvature of the main curvature 320 of the curved ultrasound transducer 30 is constant or substantially constant. In other words, the radius of curvature of the main curvature 320 of the curved ultrasound transducer 30 keeps the same curvature along its longitudinal axis.

According to another embodiment of the invention, the radius of curvature of the main curvature 320 of the curved ultrasound transducer 30 can vary along the longitudinal axis of the ultrasound hand probe $L_A$. For instance, the radius of curvature is higher on a proximal end 33 of curved ultrasound transducer 30 than it is on the distal end 34 of said curved ultrasound transducer 30. This characteristic makes it easier to orientate said curved ultrasound transducer 30 for a physician.

According to an embodiment of the invention, the curved ultrasound transducer 30 is integrated in the housing 20 of the ultrasound hand probe 10.

By integrated in the housing 20, we mean that an exterior surface of the curved ultrasound transducer is comprised in an exterior surface of the housing 20. In other words, the curved ultrasound transducer doesn't protrude from the housing 20.

Preferably, the curved transducer 30 comprises a contact surface 32. The contact surface 32 of the curved transducer 30 is configured to be placed in contact with the surface of the skin of a patient. Preferably, the contact surface 32 of the curved transducer and the outer surface of the housing 20 forms a continuous surface.

Preferably, the housing 20 encompass all exterior surfaces of the curved transducer 30 but the contact surface 32.

Preferably, the curved ultrasound transducer 30 has length comprised between 10 and 30 mm The curved transducer 30 defines a field of view of the ultrasound hand probe 10. By field of view of the ultrasound hand probe, we mean the zone in which the transducer 30 sends ultrasound waves and from which the transducer 30 receives ultrasounds. According to an embodiment, the field of view of the ultrasound hand probe 30 is comprised in a plane which perpendicular to the contact surface 32. Preferably, the field of view of the ultrasound hand probe 10 is comprised in a plane which comprises the longitudinal axis $L_A$ of the ultrasound hand probe 10. Preferably, the curved ultrasound transducer 30 has a sectorial field of view. Preferably, the angle between the lines forming the two sides of the sectoral field of view is comprised between 0.1 and 0.5 degrees. More preferably, the angle between the lines forming the two sides of the sectoral field of view is comprised between 0.2 and 0.4 degrees The curved ultrasound transducer 30 emits and receive sonic waves in the domain of ultrasound sonic waves. Preferably, the wavelength of the sonic waves emitted and received is comprised between 10 and 30 MHz. This field of wave lengths is adapted to visualize tissues of the body in various depths. More preferably, the wavelength of the sonic waves emitted and received is comprised between 18 and 20 MHz. This field of wave lengths is particularly adapted to visualize the superficial layers of the human skin, and is very convenient to assist a physician during an injection procedure in said tissues. Particularly, it permits to visualize blood vessels in these tissues and to avoid it when injecting.

The curved ultrasound transducer 30 is linked to at least one electrical connection. By electrical connection we mean a wire, a cable, a coaxial cable, a flex cable or flat flex cable.

The curved ultrasound transducer 30 is linked to at least one wire 25. The wire 25 powers the transducer by giving it electrical energy. The wire is also used to acquire the signal generated by the ultrasound curved transducer 30. Thus, the signal of the transducer 30 in response to the reception of ultrasounds can be transmitted by the wire to an external visualization device.

Accessory Device

The ultrasound hand probe 10 comprises at least one accessory device 40. The accessory device 40 comprises at least one first attach 41. The first attach 41 is configured to attach the accessory device 40 to the housing 20 of the ultrasound hand probe 10.

According to an embodiment, the first attach 41 comprises a shape that can be clipped on the housing. Preferably, the first attach 41 comprises a shape which is complementary to the shape of the housing 20. According to an embodiment, the first attach 41 forms a rail in which the housing 20 can be inserted. The rail is a good shape to easily fixed the housing 20 in the first attach. According to an embodiment, the first attach 41 comprises a clip. The clip is configured to fasten the housing 20 of the ultrasound hand probe to the accessory device 40. The clip 41 comprises at least one flexible part. The flexible part is able to deform when submitted to a strain. When inserting the housing 20 in the first attach 41, the flexible part is deformed and retract when the housing 20 is in its fastened position. To detach the housing 20 from the first attach 41, the flexible part is deformed again until the housing 20 is free. According to an embodiment, the flexible part comprises two flexible parts. The two flexible parts form the clip. The two flexible parts act as a clamp maintaining the housing 20 fixed with the accessory device.

Figure 3:
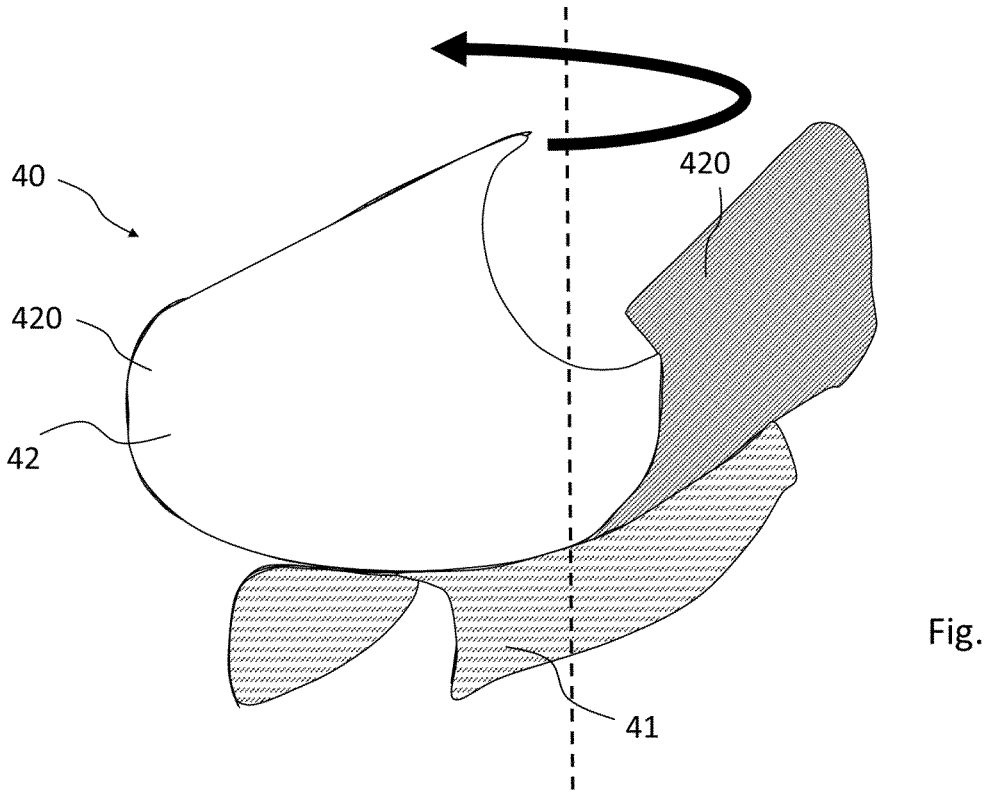
FIG. 3 is a perspective view of an accessory device according to an embodiment of the invention.

FIG. 3 presents an accessory device according to an embodiment. The first attach 41 is in the shape of a rail in which the housing 20 can be inserted. The accessory device 40 comprises a finger clip 42. The finger clip 42 has a size adapted for a finger to be inserted in. During the use of the ultrasound hand probe 10, the housing 20 is inserted in the first attach 41. As a result, the housing 20 and the curved transducer 30 are fixed to the accessory device 40. Then, the physician inserts his finger, preferably the index finger, in the finger clip 42. As a result, the ultrasound hand probe 10 is attached to the finger of the physician. In this way, the physician has both hands free. This characteristic facilitates the injection procedure.

The accessory device 40 comprises retaining wings 420. Preferably, the accessory device 40 comprises two retaining wings 420. The two retaining wings 420 are placed on the sides of the accessory device. As a result, the retaining wings 420 act as a clamp for the finger of the physician. As a result, the accessory device 40 and the ultrasound hand probe are well maintained on the finger of the physician. Alternatively, the accessory device 40 comprises a finger hole. The finger hole has a radius adapted for the introduction of a finger inside it. As a result, the accessory device is fixed to the finger of the physician when said finger is inserted in the finger hole.

FIG. 4 represents the finger hand probe 10 and the accessory device 40 of FIG. 3 installed on the finger of a physician. The figure also represents a surface 50 of the skin of a patient. The curved transducer 30 is in contact with the surface of the skin 50 of the patient in order to scan said skin and subcutaneous tissues. The physician applies a force on the finger hand probe 10 in direction to the skin of the patient to scan said skin. As a result, the hand probe 10 applies a reciprocal force $F_1$ on the finger of the physician. As shown on FIG. 4, this reciprocal force $F_1$ is inclined with respect to the main axis of the finger. That means that a large amount of the force is transmitted in alignment with the main axis of the finger. In the devices of the prior art, the reciprocal force $F_1$ tends to be perpendicular with the main axis of the finger, which implies a lot of strains and fatigue on the finger and its articulations. As a result, the finger hand probe 10 according to the invention provokes less fatigue to the physician than known devices, and facilitate the application of a force to the probe 10.

According to an embodiment, the accessory device 40 comprises a rotating accessory fastener. The rotating accessory fastener is placed between the first attach 41 and the finger clip and/or retaining wings 420. The rotating accessory fastener allows a rotation between the first attach 41 and the rest of the accessory device 40. This rotation between the first attach 41 and the finger clip and/or retaining wings 420 is showed by the arrow on FIG. 3, and the axis of rotation is showed on this figure by the vertical dotted line. As a result, the housing 20 and the curved ultrasound transducer 30 can rotate with respect to the finger of the physician when the accessory device 40 is fixed to the finger of the physician. As a result, it is possible to orientate the transducer without moving the finger of the physician. This characteristic enhances the ergonomic of the ultrasound hand probe 10.

Additionally, the rotating accessory fastener comprises a return element. The return element applies a returning torque to the first attach 41 when it not in a resting position. As a result, when the rotating accessory fastener is not in its resting position, the return element makes it rotate to come back in its initial position. This characteristic allows the physician to rotate his finger when the curved ultrasound transducer 30 is in contact with the skin of the patient without rotating the curved transducer 30, the curved ultrasound transducer coming back into place when it is no longer in contact with the skin of the patient.

The rotating accessory fastener is also compatible with the embodiments of the accessory device 40 described below.

We will present below a second embodiment of an accessory device 40 according to the invention.

The accessory device 40 has a general shape of a hockey stick. The accessory device 40 comprises a shaft 43. The first attach of the accessory device 40 is placed at an end of the shaft 43. Preferably, the main axis of the hand probe 10 is angle regarding a main axis of the shaft 43. As a result, the housing 20 and the transducer 30 can be fastened to the end of the shaft. The hockey stick shape of the accessory device 40 permits the physician to hold the ultrasound hand probe 10 between two fingers while operating. Preferably, the physician holds the shaft 43 between his index finger and his thumb. The hockey stick shape is a convenient shape for injection procedures since it allows the physician to apply a force on the skin of the patient.

We will present below a third embodiment of the accessory device 40. The accessory device 40 comprises a shaper forming "T". Preferably, the "T" of the "T" shape is placed on top of the first attach 41. The "T" has a height which is close to the height of a finger. In use, the physician places two of his fingers around the vertical bar of the "T". As a result, the fingers are maintained between the lateral bar which is on top of the "T" and the first attach 41. As a result, the ultrasound hand probe 10 is fixed to the fingers of the physician, allowing him to manipulate the ultrasound hand probe 10 freely.

Figure 6:
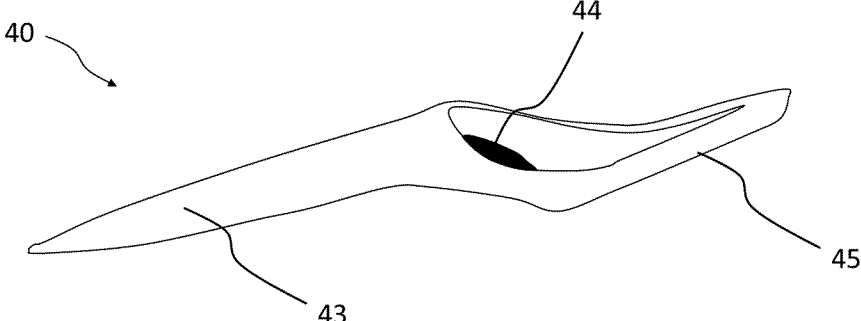
FIG. 6 is a perspective view of an accessory device according to an embodiment.
Figure 7:
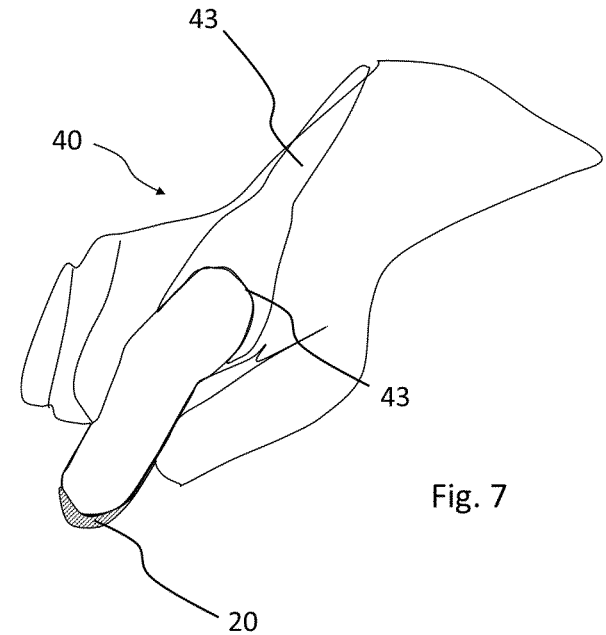
FIG. 7 is a perspective view of an ultrasound hand probe comprising the accessory device of FIG. 6 installed on a finger of a physician.
Figure 8:
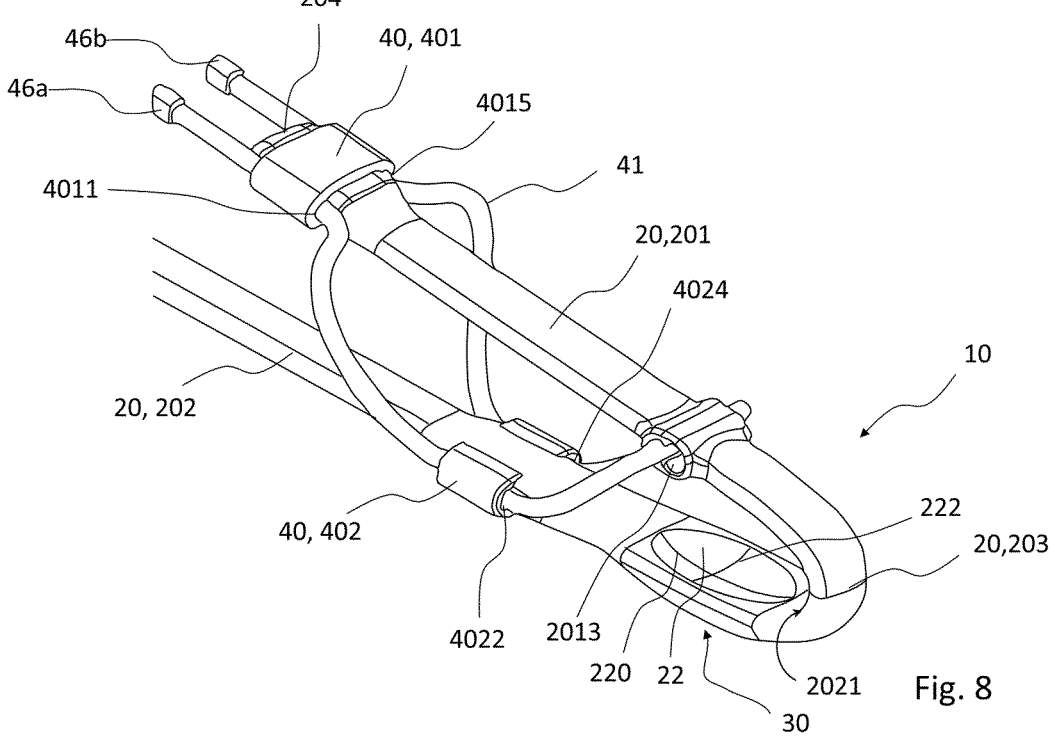
FIG. 8 is a perspective view of an ultrasound hand probe according to an embodiment of the invention.

FIG. 6 and FIG. 7 represent an accessory device according to a fourth embodiment. The accessory device 40 comprises a finger hole 44. The finger hole 44 has a size adapted for a human finger to be inserted in. Preferably, the finger hole 44 has a size adapted for the passage of an index finger. The accessory device 40 comprises a shaft 43. The shaft 43 is placed on top of the finger hole 44. The shaft 43 advantageously permits the user to manipulate the accessory device 40. The shaft 43 has the advantage of allowing a transmission of forces applied to the ultrasound hand probe 10 to the back of the hand of the user. The shaft 43 is optional and it is possible to have an accessory device 40 without the shaft 43. The accessory device 40 comprises an attach shaft 45. The attach shaft 45 comprises the first attach 41. Advantageously, the first attach 41 is a gutter. The gutter has a size adapted to receive the housing 20 and to maintain it on the accessory device 40. In use, the housing 20 is inserted in the gutter to be fixed to the accessory device 40. When the accessory device 40 is inserted on the finger of a physician, the housing 20 and the curved ultrasound transducer 30 are placed in regards with the tip of the finger of the physician. In this position, when the physician applies a force $F_1$ with his finger on the housing 20, in order to correctly apply the curved transducer 30 on the skin of the patient, the force applied on the hand of the physician is then spread between the finger of the physician, the articulation linking the finger and the hand of the physician and the back of the hand of the physician. This results in less fatigue for the physician when he manipulates the probe.

Figure 5:
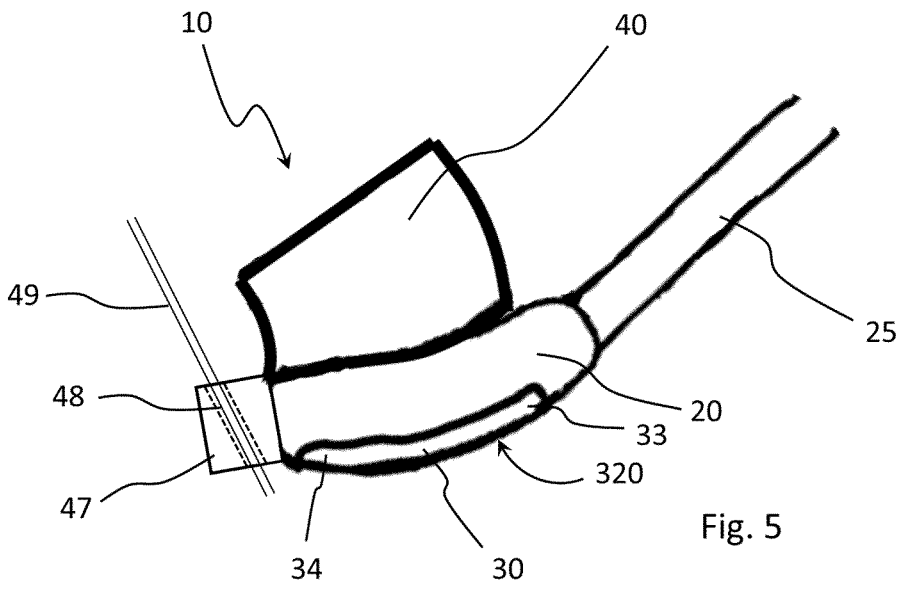
FIG. 5 is a side view of an ultrasound hand probe according to the invention comprising a needle guide.

According to an embodiment, the accessory device 40 comprises a needle guide. A finger hand probe 10 comprising an accessory device 40 comprising the needle guide 47 is represented on FIG. 5. This figure also represents a needle 49 inserted in the needle guide 47. The accessory devices 40 of all the embodiments described above can comprise a needle guide. In one embodiment we can have different orientations of the axis of the needle guide. The orientation of the needle guide may be adjustable respective to the main axis of the ultrasound probe 30, or the main axis of the housing 20. The orientation of the needle guide may be sensibly parallel to the main axis of the finger of the physician.

The needle guide 47 is preferably placed at the distal end of the accessory device 40. The needle guide 47 comprises at least one needle hole 48 or at least one needle gutter. The needle hole 48 or gutter has a diameter and size which is adapted to the passage of a needle 49. Preferably, the diameter and size are adjusted to the size of the needle 49. The needle guide 47 forms a straight path that guides the needle when it is inserted inside the needle hole 48 or gutter. Preferentially, the needle guide 47 comprises an element protruding from the accessory device 40. The needle hole 48 or gutter passes through the protrusion of the needle guide 47. An end of the needle hole 48 or gutter comes in contact or near the skin surface of the patient when the curved ultrasound transducer 30 is in contact with the surface of the skin of the patient. As a result, the needle guide 47 is adapted to guide a needle 49 during an injection procedure. This characteristic facilitates the injection procedure. Additionally, the accessory device 40 comprises one two, three or more needle guides or needle gutters. This characteristic enables to vary the sites where the needle penetrates the skin of the patient. The various needle guides or needle gutters can have different spatial orientations. This characteristic enables to guide a needle with different angles respective to the skin of the patient during the injection procedure.

According to an embodiment, the needle guide 47 is rotatable with respect to a main part of the accessory device 40. This characteristic enables the physician to adjust the point of injection with respect to the ultrasound hand probe 10. This characteristic also permits adjusting the angle penetration of the needle in the skin of the patient.

According to an embodiment, the housing 20 comprises at least one needle guide 47. The needle guide is preferably placed at the distal end of the housing 40. The needle guide 47 comprises at least one needle hole or at least one needle gutter. The needle hole 48 or gutter has a diameter and size which is adapted to the passage of a needle 49. Preferably, the diameter and size are adjusted to the size of the needle. The needle guide 47 forms a straight path that guides the needle when it is inserted inside the needle hole or gutter. Preferentially, the needle guide 47 comprises an element protruding from the housing 20. The needle hole 48 or gutter passes through the protrusion of the needle guide 47. An end of the needle hole 48 or finger comes in contact or near the skin surface of the patient when the curved ultrasound transducer 30 is in contact with the surface of the skin of the patient. As a result, the needle guide 47 is adapted to guide a needle during an injection procedure. This characteristic facilitates the injection procedure. Additionally, the housing 20 comprises one two, three or more needle holes 48 or needle gutters. This characteristic enables to vary the sites where the needle penetrates the skin of the patient. The various needle guides or needle gutters can have different spatial orientations. This characteristic enables to guide a needle with different angles respective to the skin of the patient during the injection procedure.

According to an embodiment, the needle guide of the housing 20 is rotatable with respect to a main part of the housing 20. This characteristic enables the physician to adjust the point of injection with respect to the ultrasound hand probe 10.

Visualizing Device

According to an embodiment, the ultrasound hand probe 10 is linked to a visualizing device. The visualizing device is configured to display on a screen the image representing the subcutaneous tissues of the patient. The image is obtained from the ultrasound signal acquired by the ultrasound curved transducer 30. The image displayed on the visualizing device permits the physician to be assisted during the injection procedure and to avoid blood vessels during the injection procedure. This makes the procedure safer for the patient.

In an embodiment, the housing 20 comprises electrical wires for supplying electrical energy to the curved transducer 30. Alternatively or additionally, the housing 20 comprises a battery that supplies electrical energy to the ultrasound curved transducer 30.

In an embodiment, the housing 20 comprises at least one electrical wire configured to transmit a signal acquired by the ultrasound curved transducer 30. The signal of the ultrasound curved transducer 30 is an image of the tissues scanned by the ultrasound hand probe 10. Alternatively or additionally, the ultrasound hand probe 10 is configured to transmit the signal produced by the ultrasound curved transducer 30 wirelessly. The wireless configuration of the ultrasound hand probe 10 permits to free the movements of the physician when he manipulates the probe 10, since there is no wire. According to an embodiment, the signal is transferred via a radio frequency communication. According to an embodiment, the signal is transferred via a Wi-Fi connection or a Bluetooth® connection.

Device with Laces

According to an embodiment, the ultrasound probe 10 comprises a first portion 201 and a second portion 202. The first portion 201 extends longitudinally or sensibly longitudinally along the longitudinal axis $L_A$ of the ultrasound hand probe 10. The second portion extends longitudinally or sensibly longitudinally along the longitudinal axis $L_A$ of the hand probe 10. According to an embodiment, the ultrasound hand probe 10 comprises a flexible distal portion 203. The flexible distal portion advantageously links the first portion 201 and the second portion 202. The term flexible portion 203 refers to a portion which is made in material which is able to twist or to be twisted. By being able to twist or be twisted, we refer to the ability of the flexible portion to bend or to be bent and to go back in its initial position. In other words, the flexible is deformable so that the orientation of the first portion respective to the second portion can be adjusted. As a consequence, an angle between the first portion 201 and the second portion 202 can be adjusted. As a consequence, the distance between an extremity 204 of the first portion 201 and the second portion 202 can be diminished by twisting the flexible portion 203. During the use of the hand probe 10, the user inserts his finger between the first portion 201 and the second portion 202. The tip of the finger of the user is in this position in direct contact with the curved finger base 22. By twisting the flexible portion 203, the user can shorten the distance between the first portion 201 and the second portion 202. As a consequence, the first and second portion 201, 202 surround the finger of the user and maintain the hand probe 10 on said finger. Additionally, the probe is adjustable thanks to this characteristic to size of the finger of the user.

This architecture of the probe 10 allows the probe to be secured around the finger of the user. When the user applies a force on the probe to apply it on the surface of the skin of a patient, the presence of the two portions and the placement of the probe enables the probe to stay in place on the tip of the finger of the user. This is particularly useful since usually the probe is generally placed under a glove of the user and is as a consequence difficult to put back in place when it slides on the tip of the finger. The probe according the invention doesn't slide on the tip of the finger and is easier to use.

According to an embodiment, the curved finger base 22 extends partially along a distal part of the 2021 of the second portion 202. Advantageously, the distal part 2021 of the second portion 202 has a shape which is incurved respective to the longitudinal axis of the probe. This characteristic permits the curved finger base 22 to be oriented to have a normal vector of its surface to be normal to the surface of the tip of the finger of a user when the ultrasound probe is worn by said user. According to an embodiment, the curved finger base 22 partially extends on the flexible portion 203.

According to an embodiment, the hand probe 10 comprises a lace 41. The lace 41 is configured to hold the first portion 201 and the second portion 202 together. In other words, the lace 41 is configured to maintain the first portion 201 and the second portion 202 in a tight position around the finger of the user.

Additionally or alternatively to the lace 41, the probe 10 comprises at least a fixing mean configured to attach the first portion 201 and the second portion 202. In other words, the fixing means holds the first portion 201 and the second portion 202 together. According to an embodiment, the fixing means is a holder. The fixing means can include a hook configured to attach the first portion and the second portion together. The fixing mean can include at least an elastic that applies a pressure that brings the first portion closer to the second portion. All these types of means allow the probe to be attached to the finger of the user.

Additionally or alternatively, the fixing mean comprises at least a hook and loop fastener which is configured to attach the first portion with the second portion. Preferably, the first portion comprise a textile band comprising the loops or the hooks of the hook and loop fastener, and the second portion comprises the loops or the hooks.

Additionally or alternatively, the fixing means comprises at least a magnet on the first or second portion and a piece of ferromagnetic material on the first and or second portion. According to this embodiment, the magnet permits the user to attach the first portion and the second portion together in order to maintain the probe on the finger of the user. Additionally or alternatively, the first portion and the second portion comprise at least a magnet each.

According to an embodiment, the first portion 201 comprises a first element 401. The first element comprises a first aperture 4011. The first aperture 4011 has a sized which is adapted for the lace 41 to be inserted in. In an embodiment, the size of the aperture 4011 is adjusted to a diameter of the lace. As a consequence, the lace is maintained in position respective to the first aperture when it is inserted inside it, thus being movable in it when a sufficient force is applied to it. In an embodiment, the first aperture 4011 is formed entirely in the first element 401. In other words, the first aperture 4011 has the shape of a hole. In an embodiment, the first aperture 4011 is formed by a space between the first element 401 and the first portion 201.

According to an embodiment, the second portion 402 comprises a second element 402. The second element 402 comprises a second aperture 4022. The second aperture 4022 has a sized which is adapted for the lace 41 to be inserted in. In an embodiment, the size of the aperture 4022 is adjusted to a diameter of the lace. As a consequence, the lace is maintained in position respective to the second aperture when it is inserted inside it, thus being movable in it when a sufficient force is applied to it. In an embodiment, the second aperture 4022 is formed entirely in the second element 402. In other words, the second aperture 4022 has the shape of a hole. In an embodiment, the second aperture 4022 is formed by a space between the second element 402 and the second portion 202.

According to an embodiment, the first portion 201 comprises a third aperture 2013. The third aperture 2013 forms a hole in the first portion 201. The third aperture 2013 has a sized which is adapted for the lace 41 to be inserted in. In an embodiment, the size of the aperture 2013 is adjusted to a diameter of the lace. As a consequence, the lace is maintained in position respective to the first aperture when it is inserted inside it, thus being movable in it when a sufficient force is applied to it. In an embodiment, the second aperture 4022 is formed entirely in the second element 402. According to an embodiment, the aperture has a main axis which is sensibly perpendicular or perpendicular to the longitudinal axis $L_A$ of the hand probe 10. According to an embodiment, the third aperture 2013 comprises two holes having each one a principal axis. The sections of the two holes around their principal axis are secant. Additionally, one of the two holes has a diameter which is bigger than the diameter of the other one. The hole with the shorter diameter of the two having a diameter adjuster to be sensibly smaller than the diameter of the lace 41. In that way, the lace 41 can be adjusted in the third aperture 2013 when it is inserted in the larger hole, and can be blocked in position respective to the first portion 201 when it is inserted in the hole with the shorter diameter. Advantageously, the third aperture 2013 comprises a narrow section between the two holes. The narrow section allows the lace 41 to be blocked in position when it is inserted in the hole with the shorter diameter.

According to an embodiment. The second element 402 comprises a fourth aperture 4024. The second aperture 4022 has a sized which is adapted for the lace 41 to be inserted in. In an embodiment, the size of the fourth aperture 4024 is adjusted to a diameter of the lace. As a consequence, the lace is maintained in position respective to the fourth aperture when it is inserted inside it, thus being movable in it when a sufficient force is applied to it. In an embodiment, the fourth aperture 4024 is formed entirely in the second element 402. In other words, the fourth aperture 4024 has the shape of a hole. In an embodiment, the fourth aperture 4024 is formed by a space between the second element 402 and the second portion 202.

According to an embodiment, the first element 401 comprises a fifth aperture 4015. The fifth aperture 4015 has a sized which is adapted for the lace 41 to be inserted in. In an embodiment, the size of the aperture 4015 is adjusted to a diameter of the lace. As a consequence, the lace is maintained in position respective to the fifth aperture when it is inserted inside it, thus being movable in it when a sufficient force is applied to it. In an embodiment, the fifth aperture 4015 is formed entirely in the first element 401. In other words, the fifth aperture 4015 has the shape of a hole. In an embodiment, the fifth aperture 4015 is formed by a space between the first element 401 and the first portion 201.

According to an embodiment, the lace 41 comprises a first blocking element 46a. The first blocking element 46a is fixed to an extremity of the lace 41. The first blocking element 46a blocks the translation of the lace 41 when it arrives in contact with the first aperture 4011. In other words, it has a size which is bigger than the size of the first aperture so that it can't pass through it. This characteristic avoids the extremity of the lace 41 to pass through the first aperture 4011 so that the lace 41 stays in place in the aperture.

According to an embodiment, the lace 41 comprises a second blocking element 46b. The second blocking element 46b is fixed to another extremity of the lace 41. The second blocking element 46b blocks the translation of the lace 41 when it arrives in contact with the fifth aperture 4015. In other words, it has a size which is bigger than the size of the fifth aperture 4015 so that it can't pass through it. This characteristic avoids the other extremity of the lace 41 to pass through the fifth aperture 4015 so that the lace 41 stays in place in the aperture.

According to an embodiment, the first aperture 4011 and the fifth aperture 4015 are placed on two opposite sides of the first portion 201 regarding the longitudinal axis $L_A$ of the hand probe 10. This characteristic enhances the tightening of the probe on the finger of the user to be done on both sides of it. In this way, the fixation on the finger is stable.

According to an embodiment, the second aperture 4022 and the fourth aperture 4024 are placed on two opposite sides of the second portion 20 regarding the longitudinal axis $L_A$ of the hand probe 10. This characteristic enhances the tightening of the probe on the finger of the user to be done on both sides of it. In this way, the fixation on the finger is stable.

According to an embodiment, the first element 401 is clipped on the first portion 201. Advantageously, the second element 402 is clipped on the second portion 202. According to an embodiment, the first element 401 is integral to or integrated in the first portion 201. According to an embodiment, the second element 402 is integral to or integrated in the second portion 402.

According to an embodiment, the curved finger base 22 comprises a second curvature. The second curvature is oriented in a plane which is perpendicular or slightly perpendicular to the main axis $L_A$ of the hand probe 10. In other words, the two curvatures permit to form a bowl which has the shape of the tip of a finger. This characteristic permits to have a probe which is really comfortable to use and is adjusted to the tip of the finger of the user.

Injection Procedure

The invention also concern method for injecting a substance and/or a medical device under the skin of a patient. The substance injected can be a fluid like a treatment fluid. This substance can also be any possible filler, no matter if the filler is in a fluid or gel form or any other form. The method also concerns the injection of any medical device under the skin, for example the placement of a thread.

Preferentially, the method for injecting a substance and/or a medical device is realized with the ultrasound hand probe according to the invention.

The method for injecting a substance and/or a medical device under the skin of a patient comprises the steps of:

fastening the first attach 41 of the accessory device 40 to the housing 20 of the ultrasound hand probe 10, inserting a finger in the accessory device 40 in order to fasten the accessory device to the finger, the finger base 22 of the housing 20 being placed in contact with the tip of the finger, placing the curved ultrasound transducer 30 comprised in the housing 20 in contact with the skin of a patient, the curved ultrasound transducer 30 being configured to acquire the ultrasound signal and transmit said ultrasound signal to an external visualizing device, the curved ultrasound transducer 30 scanning the subcutaneous tissues of the skin of the patient, visualising an image of the subcutaneous tissues of the patient on the external visualizing device, said image being extracted from the ultrasound signal by said external visualizing device, inserting a needle of a syringe in the skin of the patient in the region of the skin that has been scanned by the ultrasound curved transducer 30, and injecting a treatment liquid under the skin of the patient with the syringe.

All the characteristics previously described for the ultrasound hand probe 10 concern also the method according to the invention.

According to an embodiment, the ultrasound probe is directed to assist a physician during an anaesthesiology procedure. For instance, it can help the physician visualise the site of the injection of a medication for anaesthesia.

According to an embodiment, the ultrasound probe is directed to assist a physician during angiology procedures. For instance, the ultrasound probe can help the physician visualize the path of blood vessels on every part of the body of a patient.

According to an embodiment, the ultrasound probe can assist a physician during an emergency medicine procedure. By this way it can help the physician visualize hidden parts of the body of the patient during this kind of procedures.

According to an embodiment, the ultrasound probe helps the physician to visualize hemodynamic.

According to an embodiment, the ultrasound probe helps the physician visualize female and male urinary tract during urology procedures.

According to an embodiment, the ultrasound probe can assist a physician during medical procedures or interventions on the penis and the scrotum of a patient.

According to an embodiment, the ultrasound probe assists a physician during rheumatology procedures. According to an embodiment, it can help the physician visualize articulations to help him treat musculoskeletal troubles.

According to an embodiment, the ultrasound probe assists a physician during sport medicine and orthopedic procedures. The advantage is to obtain precise images of parts of the body of the patient to help the physician perform the procedure.

According to an embodiment, the ultrasound probe assists a physician during endocrinology procedure by providing him ultrasound images of the body of the patient.

According to an embodiment, the ultrasound probe assists a physician during gynaecology procedure by providing him ultrasound images of the body of the patient, especially images of cavities of the patient.

According to an embodiment, the ultrasound probe is used in veterinary medicine. The ultrasound probe helps the physician to obtain images of the body of the animal to help him during these procedures.

According to an embodiment, the ultrasound probe assists a physician during neurosurgery procedure by providing him ultrasound images of the body of the patient.

According to an embodiment, the ultrasound robe assists a physician during an ophthalmology procedure and/or treatment.

REFERENCES

10: ultrasound hand probe
20: housing of the ultrasound hand probe
201: first portion
2013: third aperture
202: second portion
2021: distal part of the second portion
203: flexible distal portion 22: curved finger base
220: first curvature of the finger base
222: second curvature of the curved finger base
23: proximal end of the housing
24: distal end of the housing
25: electrical wire
$L_4$: longitudinal axis of the ultrasound hand probe
30: curved ultrasound transducer
320: main curvature of the curved ultrasound transducer
32: contact surface of the curved ultrasound transducer
33: proximal end of the curved transducer
34: distal end of the curved transducer
40: accessory device
401: first element of the accessory device
4011: first aperture
4015: fifth aperture
402: second element of the accessory device
4022: second aperture
4024: fourth aperture
41: first attach of the accessory device
42: finger clip 420: retaining wings
43: shaft of the accessory device
44: finger hole of the accessory device
45: attach shaft
46a: first blocking element
46b: second blocking element
47: needle guide
48: needle hole
49: needle

The invention claimed is:

1. An ultrasound hand probe intended to be placed on a ventral part of a finger, configured to emit and receive ultrasound, said ultrasound hand probe comprising:
a curved ultrasound transducer,
a housing attached to the curved ultrasound transducer, the curved ultrasound transducer being arranged on a distal end of the housing, the housing comprising:
a curved finger base comprising a curvature along a longitudinal axis of the ultrasound hand probe,
electrical connections for:
supplying power to the curved ultrasound transducer, and
transmitting a signal produced by the curved ultrasound transducer,
at least one accessory device comprising at least one first attach to fasten said at least one accessory device with the ultrasound hand probe,
wherein the curved finger base has a radius of curvature comprised between 2 centimetres and 5 centimetres in a longitudinal plane of the ultrasound hand probe.

2. The ultrasound hand probe according to claim 1, wherein the housing comprises a first portion and a second portion configured to extend along a finger axis, said first portion and second portion being linked by a flexible distal portion.

3. The ultrasound hand probe according to claim 1, wherein the curved finger base comprises a second curvature in a plane which is perpendicular to the longitudinal axis of the ultrasound hand probe.

4. The ultrasound hand probe according to claim 1, wherein the at least one accessory device is a first accessory device comprising a finger clip.

5. The ultrasound hand probe according to claim 1, wherein the at least one accessory device is a second accessory device comprising a distal aperture configured to guide a needle.

6. The ultrasound hand probe according to claim 5, wherein the distal aperture is rotatable with respect to the ultrasound hand probe, allowing to adapt an angle of injection of the needle.

7. The ultrasound hand probe according to claim 1, wherein the at least one accessory device is a third accessory device comprising a hockey stick shape.

8. The ultrasound hand probe according to claim 1, wherein the at least one accessory device is a fourth accessory device comprising a shape forming a "T" so that the ultrasound hand probe is maintainable between two fingers.

9. The ultrasound hand probe according to claim 1, wherein the at least one accessory device comprises a rotating accessory fastener allowing a variable orientation of the housing relative to the at least one accessory device along a rotation axis.

10. The ultrasound hand probe according to claim 9, wherein the rotating accessory fastener comprises a return element allowing an automatic return of the rotating accessory fastener in its initial position.

11. The ultrasound hand probe according to claim 1, wherein the at least one accessory device comprises retaining wings for maintaining a finger between said retaining wings.

12. The ultrasound hand probe according to claim 1, wherein the housing has an oval transversal section or an ellipse-shaped transversal section.

13. The ultrasound hand probe according to claim 1, wherein the curved finger base has a radius of curvature comprised between 1 centimetre and 5 centimetres in a transversal plane of the ultrasound hand probe.

14. The ultrasound hand probe according to claim 1, wherein the curved ultrasound transducer has a sectorial field of view, the sectorial field of view covering an angle superior than 20 degrees.

15. The ultrasound hand probe according to claim 1, wherein a frequency of ultrasounds emitted by the curved ultrasound transducer is between 10 and 30 Mhz.

16. The ultrasound hand probe according to claim 1, wherein the ultrasound hand probe is configured to transmit data acquired by the ultrasound hand probe wirelessly.

17. An ultrasound hand probe intended to be placed on a ventral part of a finger, configured to emit and receive ultrasound, said ultrasound hand probe comprising:
a curved ultrasound transducer,
a housing attached to the curved ultrasound transducer, the curved ultrasound transducer being arranged on a distal end of the housing, the housing comprising:
a curved finger base comprising a curvature along a longitudinal axis of the ultrasound hand probe,
electrical connections for:
supplying power to the curved ultrasound transducer, and
transmitting a signal produced by the curved ultrasound transducer,
at least one accessory device comprising at least one first attach to fasten said at least one accessory device with the ultrasound hand probe,
wherein the housing comprises a first portion and a second portion configured to extend along a finger axis, said first portion and second portion being linked by a flexible distal portion, and
wherein the at least one accessory device comprises a lace configured to attract the first and second portions and bring said first portion and said second portion closer to each other.

18. The ultrasound hand probe according to claim 17, wherein a first element comprising at least a first aperture is attached to the first portion of the housing, wherein a second element comprising at least a second aperture is attached to the second portion of the housing, and wherein the lace passes through at least the first and the second apertures of the first and the second element, said lace being movable in the second aperture.

19. The ultrasound hand probe according to claim 18, wherein the first portion comprises at least a third aperture, the lace passing through the third aperture.

20. The ultrasound hand probe according to claim 19, wherein the first element comprises a fourth aperture and the second element comprises a fifth aperture, the lace passing through the fourth aperture and the fifth aperture.

21. The ultrasound hand probe according to claim 20, wherein the first aperture is configured to hold the lace in position, the lace being movable in said first aperture if a sufficient force is applied to it.

\* \* \* \* \*